(12) United States Patent
Charaf et al.

(10) Patent No.: US 6,528,472 B2
(45) Date of Patent: Mar. 4, 2003

(54) ANTIMICROBIAL COMPOSITIONS CONTAINING QUATERNARY AMMONIUM COMPOUNDS, SILANES AND OTHER DISINFECTANTS WITH FURANONES

(75) Inventors: Ursula K. Charaf, Land O'Lakes, WI (US); Richard W. Avery, High Wycombe (GB)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/986,301

(22) Filed: Nov. 8, 2001

(65) Prior Publication Data

US 2002/0111282 A1 Aug. 15, 2002

Related U.S. Application Data

(60) Provisional application No. 60/249,253, filed on Nov. 17, 2000.

(51) Int. Cl.[7] .............................. C11D 3/48; C11D 1/62
(52) U.S. Cl. .................. 510/391; 510/199; 510/238; 510/247; 510/382; 510/384; 510/504
(58) Field of Search ................................ 510/199, 238, 510/247, 382, 384, 391, 504

(56) References Cited

U.S. PATENT DOCUMENTS

| | | | |
|---|---|---|---|
| 5,411,585 A | 5/1995 | Avery et al. | |
| 5,906,825 A | 5/1999 | Seabrook, Jr. et al. | |
| 6,060,046 A | 5/2000 | Steinberg et al. | |
| 6,075,019 A | 6/2000 | Uhr et al. | |
| 6,087,319 A | 7/2000 | Norman | |
| 6,184,195 B1 | 2/2001 | Cheung et al. | |

FOREIGN PATENT DOCUMENTS

| | | | |
|---|---|---|---|
| WO | 96/01294 | 1/1996 | |
| WO | 96/29392 | 9/1996 | |
| WO | 99/53915 | 10/1999 | |
| WO | 99/54323 | 10/1999 | |
| WO | WO 00/54587 A | 9/2000 | .......... A01N/25/08 |
| WO | 01/43739 | 6/2001 | |
| WO | 01/68090 | * 9/2001 | |
| WO | 01/68091 | 9/2001 | |
| WO | WO 01/85664 | 11/2001 | .......... C07C/49/00 |

OTHER PUBLICATIONS

Schauder, et al. "The LuxS Family of Baterial Autoinducers: Biosynthesis of a Novel Quorum–Sensing Signal Molecule", Molecular Microbiology, vol. 41, 2, pp. 463–476, Jul. 2001.

Schauder, et al. "The Lux–S Family of Baterial Autoinducers: Biosynthesis of a Novel Quorum Sensing Signal Molecule", ASM Conference on Cell–Cell Communication in Bacteria, American Society for Microbiology, Jul. 6–9, 2001, Snowbird, Utah.

* cited by examiner

*Primary Examiner*—Charles Boyer

(57) ABSTRACT

A synergistic antimicrobial composition includes an effective amount of at least one furanone, together with other disinfectants, such as, for example, an effective amount of at least one organosilane with quaternary ammonium functionality, and/or an effective amount of at least one quaternary ammonium compound. Additionally, biguanides and disinfectant amines also may be advantageously combined with furanones in an antimicrobial composition.

19 Claims, 9 Drawing Sheets

(2 of 9 Drawing Sheet(s) Filed in Color)

FURANONE 10

FURANONE 12

FURANONE 13

FURANONE 15

FURANONE 14

FURANONE 16

FURANONE 17

ANTIMICROBIAL COMPOSITIONS CONTAINING QUATERNARY AMMONIUM COMPOUNDS, SILANES AND OTHER DISINFECTANTS WITH FURANONES

RELATED APPLICATION

This application claims the benefit of U.S. Provisional Application No. 60/249,253, filed Nov. 17, 2000.

FIELD OF THE INVENTION

This invention relates to antimicrobial compositions. In particular, this invention relates to synergistic antimicrobial compositions offering superior performance, containing combinations of furanones with other disinfectants, such as, for example, quaternary ammonium compounds and/or organosilanes with quaternary ammonium functionality ("quaternized organosilanes"). Additionally, biguanides and disinfectant amines also may be advantageously combined with furanones in an antimicrobial composition.

BACKGROUND OF THE INVENTION

Mold, mildew and bacterial contamination are undesirable on many types of surfaces. Control of such biological fouling has largely been based on the use of biocides that may have a harmful effect on the environment. However, the use of natural biocides or derivatives thereof that are environmentally acceptable is becoming increasingly desirable and necessary.

The bacterial properties of quaternary ammonium compounds are generally known. Such compounds have been used extensively in cleaning compositions for domestic and industrial applications. However, it would be preferable to use small amounts of these compounds in cleaning compositions since they can be harmful to the environment in large amounts.

Quaternized organosilanes also have antimicrobial activity, and can be used to treat mold and mildew in buildings; however, it is necessary to stabilize them before they can be used in cleaning compositions. U.S. Pat. No. 5,411,585 to Avery, et al. teaches that certain organosilanes containing hydrolyzable groups, especially quaternized organosilanes, can form clear solutions in aqueous media that are stable over extended periods of time. These solutions are formed without the use of emulsion technology involving the application of high shear forces, by further including a water soluble organic, non-silicon quaternary ammonium compound along with nonionic, amphoteric, sarcosine anionic or certain cationic surfactants. U.S. Pat. No. 6,087,319 also teaches that organosilanes, including quaternized organosilanes, can be stabilized using saccharides, sometimes with an additional nonionic co-surfactant. Stabilized organosilanes remain stable over a broad pH range. They can then be particularly useful as coupling agents in household and industrial cleaning compositions where an antimicrobial and soil-releasing substrate is desired. However, given that quaternized organosilanes are expensive, it may not be economical to use this compound exclusively to impart antimicrobial activity to a household or industrial cleaning solution.

Certain furanones, particularly halogenated furanones, which can be derived from natural sources, such as seaweed, or synthesized, are also known to inhibit the growth of microorganisms.

U.S. Pat. No. 6,060,046 relates to an antifouling composition that comprises an effective amount of a halogenated furanone compound having a specified structure. The compounds all share a basic carbon skeleton consisting of a furanone moiety with a butyl side chain at the 3-position and other substitutions at other points on the basic structure. The antifouling compositions are intended to be used to combat the settlement and subsequent growth of marine organisms on submerged surfaces such as boat hulls or oil and gas platforms. These furanones are said to be extremely active against fouling organisms, for example, such as invertebrates and bacteria.

International Patent Publication No. WO 96/29392 is directed to methods and culture media including furanones for inhibiting homoserine lactone (HSL) and/or acylated homoserine lactone (AHL) regulated processes in microorganisms, including bacteria, fungi and algae. The disclosed compounds are structurally related furanones having a basic furanone moiety with an alkyl side chain at the 3-position of the basic structure. The basic structure is preferably halogenated and has other possible substitutions that are disclosed in the patent document.

International Patent Publication No. WO 99/53915 discloses a method of inhibiting the growth of Gram positive bacteria using one or more furanones having a specified formula.

International Patent Publication No. WO 99/54323 demonstrates diverse side-chain functionalizations of fimbrolides (halogenated 3-alkyl-5-methylene-2(5H)-furanones).

International Patent Publication No. WO 01/68091 discloses that certain selected furanone compounds are suitable as antifungal agents for a range of fungi.

International Patent Publication No. WO 01/43739 provides compositions and methods for inhibiting two-component signal transduction systems with halogenated furanones and related 3-haloalkenones.

Furanone-like 5-membered ring compounds recently have been identified in varied microorganisms (i.e., not only marine microorganisms), as being universal signal compounds that, like acetylated homoserine lactones, are involved in quorum sensing, namely the process that allows microorganisms to assess their environment, such as the density of organisms that surround them. Unlike acetylated homoserine lactones, however, these furanone-like 5-membered ring compounds appear not to be species-specific, and they appear to be active in very diverse types of microorganisms. (See S. Schauder, et al., "The LuxS-Family of Bacterial Autoinducers: Biosynthesis of a Novel Quorum Sensing Signal Molecule", Poster Abstract presented at "Cell-Cell Communication in Bacteria" Meeting in Snowbird, Utah, Jul. 6–9, 2001.)

Consequently, halogenated furanone compounds, in particular, and possibly other structurally similar compounds, may act by competitively inhibiting these furanone-like 5-membered ring signal compounds. As the furanone-like signals are recognized by different types of organisms, the inhibitory activity of, for example, the halogenated furanone compounds (and other compounds like them), interfere with growth and biofilm formation of various Gram positive and Gram negative bacteria, as well as of yeasts and fungi. Therefore, hereinafter, when using the term "furanone" in this application, we have in mind those furanones, such as halogenated furanones and furanones noted in the patent documents discussed earlier, which exhibit such inhibitory activity.

While furanones are more friendly to the environment since they are derived from a naturally-occurring group of compounds that can be isolated from red marine algae, such as *Delisea fimbriata, Delisea elegans* and *Delisea pulchra*, they can be expensive to use in the amounts necessary to be effective in antimicrobial cleaning compositions.

SUMMARY OF THE INVENTION

Accordingly, there is a need for antimicrobial compositions that are friendly to the environment, effective and relatively economical to manufacture on a commercial scale for both domestic and industrial cleaning applications.

Surprisingly, we have found that an unexpectedly high level of synergy occurs in antimicrobial compositions that contain at least one furanone in combination with other disinfectants, such as, for example, at least one quaternary ammonium compound and at least one quaternized organosilane. The synergy is evidenced by the small quantities of each of these compounds that need to be used to produce an effective antimicrobial composition. The necessary overall amount of the compounds is less than that which would be required if any of the compounds were to be used on their own. In particular, it is possible to use small amounts of furanones, which can be expensive but are environmentally friendly, with small amounts of quaternized organosilanes which are also expensive, and quaternary ammonium compounds which are not particularly environmentally friendly but are quite effective antimicrobials. We believe that a similar type of synergy would be apparent in antimicrobial compositions that contain at least one furanone in combination with at least one quaternary ammonium compound or at least one quaternized organosilane. Similarly, we believe that biguanides and disinfectant amines also may be advantageously combined with furanones in an antimicrobial composition.

Accordingly, one aspect of the invention provides a composition comprising: (a) a sparing amount of at least one furanone; and (b) a sparing amount of at least one stable quaternized organosilane, wherein the amount of each of components (a) and (b) is sufficient to form, in combination, a synergistic, antimicrobial composition. Alternatively, another aspect of the invention provides a composition comprising: (a) a sparing amount of at least one furanone; (b) a sparing amount of at least one quaternized organosilane; and (c) a sparing amount of at least one quaternary ammonium compound, wherein the amount of each of components (a), (b) and (c) is sufficient to form, in combination, a synergistic antimicrobial composition. In yet another alternative embodiment, a composition of the invention comprises: (a) a sparing amount of at least one furanone; and (b) a sparing amount of at least one quaternary ammonium compound, wherein the amount of each of components (a) and (b) is sufficient to form, in combination, a synergistic antimicrobial composition.

In still another alternative embodiment, a composition of the invention comprises: (a) a sparing amount of at least one furanone; and (b) a sparing amount of at least one disinfectant selected from the group consisting of a quaternized organosilane, a quaternary ammonium compound, a disinfectant amine, and a biguanide, wherein, the amount of each of components (a) and (b) is sufficient to form, in combination, a synergistic antimicrobial composition.

Our invention also provides a method of cleaning a surface, or a reservoir or conduit that is fluid-filled using a synergistic antimicrobial composition comprising any of the combinations of components described above.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1A:
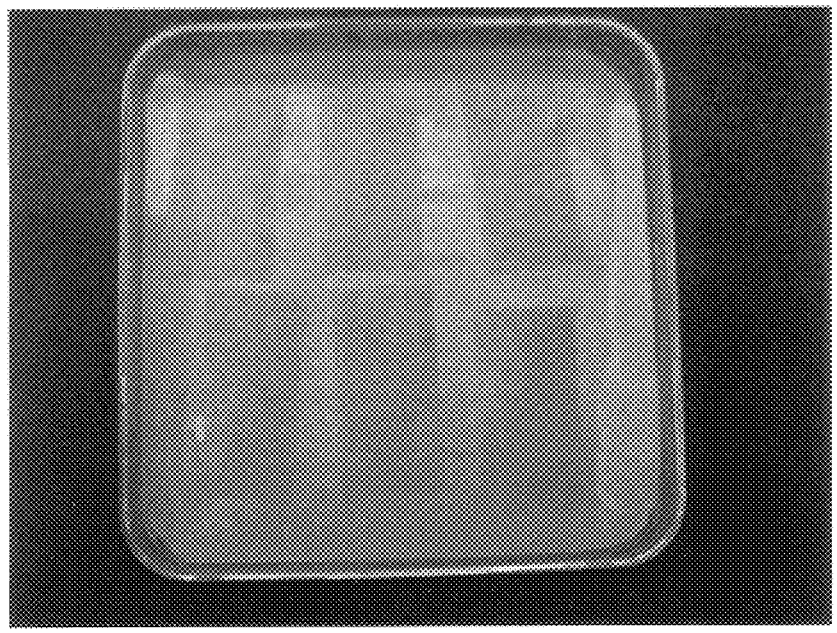
FIGS. 1A, 1B and 1C are photographic images of the zone of inhibition results obtained in the zone of inhibition assay using *Staphylococcus aureus* described in Example 3.

Molds (fungi) and yeasts can become a significant nuisance in most domestic and industrial contexts. The following fungi and yeast species represent major problem organisms in the domestic context: Aureobasidium species (e.g., such as *Aureobasidium pullulans*), Alternaria species (e.g., such as *Alternaria alternata*), Penicillium species (e.g., such as *Penicillium digitatum*), Aspergillus species (e.g., such as *Aspergillus niger*), Stachybotrys species, (e.g., such as *Stachybotrys atra*), Trichophyton species (e.g., such as *Trichophyton rubrum*), Cladosporium species (e.g., such as *Cladosporium cladosporioides*), and Candida species (e.g., such as *Candida albicans*). Fungi may be found and sporulate on damp household surfaces (e.g., in the bathroom), and so it is useful to destroy them since they may cause health problems. *Alternaria alternata,* for example, may only occasionally be found in households, but can cause asthma and allergic reactions. *Cladosporium cladosporioides* and other fungi may be pathogenic, as are yeasts such as *Candida albicans*.

Bacteria, such as Staphylococcus species (e.g., such as *Staphylococcus aureus*), Escherichia species (e.g. such as *Escherichia coli*), Salmonella species (e.g., such as *Salmonella enteritidis*), Shigella species (e.g., such as *Shigella sonnet*), Klebsiella species (e.g., such as *Klebsiella pneumoniae*), Proteus species (e.g., such as *Proteus mirabilis*), Pseudomonas species (e.g., such as *Pseudomonas aeruginosa*), Enterobacter species (e.g., such as *Enterobacter aerogenes*) and others are opportunistic pathogens and thus may be problematic in the domestic and industrial contexts.

Consequently, fungi, bacteria and other biofouling organisms must be controlled using effective antimicrobial cleaning solutions to keep home and industrial environments aesthetically pleasing, healthy and safe.

We have surprisingly formulated a powerful, synergistic antimicrobial composition that requires remarkably small amounts (i.e., sparing amounts) of active ingredients (compared to that which has been used in the past) to be effective. Because such small amounts of active ingredients need to be used for these inventive synergistic antimicrobial compositions, the compositions are environmentally friendly. These compositions have properties that include those of the separate compounds but go beyond them in efficacy and scope of application. The extremely low levels, and hence increased efficacy, of the active compounds or ingredients make this invention very desirable.

Specifically, in one embodiment, our invention is directed to a novel composition that combines furanones together with other disinfectants, such as, quaternary ammonium compounds and/or quaternized organosilanes, such that lesser quantities of furanone, quaternary ammonium compounds and/or quaternized organosilanes than would normally be necessary for an antimicrobial composition are used to achieve excellent cleaning and disinfecting results. Higher concentrations of these components can be used if this is desired for certain applications. Higher concentrations of each component might be used, for example, if a concentrated product to be diluted by the consumer were to be prepared. Concentrated products also are used in solid toilet bowl cleaners, such as in toilet bowl rim blocks that are particularly popular in Europe. These products dissolve in the flush water of a toilet. In any case, however, the amounts of active ingredients should be used sparingly.

More specifically, the amount of furanones to be used in the synergistic antimicrobial composition of this invention is between about $1.0 \times 10^{-7}$ weight percent of the composition (i.e., 1 µg/L) and up to about 0.5 weight percent of the composition (i.e., 5000 mg/L). The higher end of this stated range might be used to prepare a concentrated product that would be diluted prior to use. For non-concentrated products, the amount of furanone to be used in this invention is preferably between about 0.00001 weight percent and about 0.01 weight percent of the composition, more preferably between about 0.0005 weight percent and about 0.005 weight percent of the composition, and most preferably about 0.001 weight percent of the composition.

If used, the amount of quaternized organosilane should be between about 0.001 weight percent and about 5.0 weight percent of the composition. The higher end of this range might apply if the composition were formulated as a concentrate, for example, to be dilutable or automatically dischargeable as an automatic toilet bowl cleaner. For non-concentrated products, the amount of quaternized organosilane to be used in this invention is preferably between about 0.001 weight percent and about 3.0 weight percent of the composition, more preferably, between about 0.03 weight percent and about 0.22 weight percent of the composition. Most preferably, the amount of quaternized organosilane should be about 0.15 weight percent of the composition.

If used, the amount of quaternary ammonium compound should be between about 0.01 weight percent and about 10.0 weight percent of the composition. As with the other components, the higher end of this stated range of quaternary ammonium compound might be used to prepare a concentrated product that would be diluted prior to use. For non-concentrated products, the amount of quaternary ammonium compound to be used in this invention is preferably between about 0.01 weight percent and about 1.0 weight percent of the composition, and more preferably between about 0.1 weight percent and about 0.5 weight percent of the composition. Most preferably, the amount of quaternary ammonium compound to be used is about 0.22 weight percent of the composition.

U.S. Pat. Nos. 5,411,585 and 6,087,319, which are incorporated herein by reference in their entirety, set out methods by which a quaternized organosilane can be stabilized, namely, using: (1) a quaternary ammonium compound and at least one nonionic, amphoteric, anionic (i.e., sarcosine-based), and cationic surfactants; or (2) using a saccharide-based surfactant and optionally an additional nonionic co-surfactant. It should be noted that a stabilizer, such as a quaternary ammonium compound, a saccharide-based surfactant or another surfactant is often necessary for water-based formulations. However, if a formulation contains a substantial amount of solvent, such as isopropanol (as shown in Table 3 below) or ethanol, then one of the mentioned stabilizers may not be required.

By one method, if a three-component composition is to be formed containing a quaternized organosilane, a quaternary ammonium compound and a furanone, these components can be combined in the following manner. With good stirring, a quaternary ammonium compound and any necessary surfactants and solvents can be combined. A quaternized organosilane can be added thereafter, followed by a furanone. It should be noted, however, that the addition order is not critical.

However, if a quaternized organosilane is combined with a furanone to obtain a synergistic antimicrobial composition and a quaternary ammonium compound is not added, the quaternized organosilane could nonetheless still be stabilized using the method described in U.S. Pat. No. 6,087,319 noted above. Alternatively, the quaternized organosilane could be stabilized using a solvent or a surfactant in appropriate amounts. Suitable surfactants include those set out in U.S. Pat. Nos. 5,411,585 and 6,087,319. Useful solvents include, for example, alcohols (such as isopropanol or ethanol), glycols (such as dipropylene glycol n-butyl ether), and alcohol amines (such as ethanolamine). Useful surfactants include, for example, a nonionic surfactant such as PLURAFAC® (made by BASF Aktiengesellschaft) which is a fatty alcohol alkoxylate, or glucosides. Once the quaternized organosilane is stabilized, a furanone could be added thereafter by stirring to produce a synergistic antimicrobial composition.

Since furanones are generally in crystalline form, they are preferably added to the composition in small amounts of ethanol or another suitable solvent. For example, since Furanone 30 is sparingly soluble in water, this furanone might be added in water.

Examples of quaternized organosilane compounds that can be used in this invention are described in U.S. Pat. No. 5,411,585. The quaternized organosilanes useful in the present invention fall within a group of water soluble organosilanes of the formula:

wherein:
  A is —OH or a hydrolyzable group;
  B is an alkyl group from 1 to 4 carbon atoms;
  X has a value of 0, 1 or 2, and
  D is (i) a hydrocarbon group of from 1 to 4 carbon atoms; (ii) a phenyl group; or (iii) a nonionic or cationic, substituted—hydrocarbon group containing at least one nitrogen group or salts of such substituted—hydrocarbon groups.

Preferably, the quaternized organosilane compound is 3-(trimethoxysilyl)propyldimethyloctadecyl ammonium chloride having the formula $(CH_3O)_3SiCH_2CH_2CH_2N^+(CH_3)_2(C_{18}H_{37})Cl^-$ (sold commercially by Aegis Environments of Midland, Mich., under the name AEM 5772 Antimicrobial MUP), or 3-(trimethoxysilyl)-propylmethyldi(decyl) ammonium chloride having the formula $(CH_3O)_3SiCH_2CH_2CH_2N^+(CH_3)(C_{10}H_{21})_2Cl^-$.

A useful description of quaternary ammonium compounds that can be used in this invention also is described in U.S. Pat. No. 5,411,585. For example, one or more of the following quaternary ammonium compounds could be used: didecyl dimethyl ammonium chloride, dioctyl dimethyl ammonium chloride, octyl decyl dimethyl ammonium chloride, benzalkonium chloride (i.e., which is a mixture of benzyl alkyl dimethyl ammonium chlorides), or alkyl benzyl alkyl dimethyl ammonium chloride. It would be preferable but certainly not necessary to use a quaternary ammonium compound such as benzalkonium chloride or didecyl dimethyl ammonium chloride.

Furanone compounds as a class, examples of which are set out in FIGS. 2 to 8, and that are described in more detail in U.S. Pat. No. 6,060,046, International Patent Publication No. WO 96/29392, International Patent Publication No. WO 99/53915, International Patent Publication No. WO 99/54323, and International Patent Publication No. WO 01/68091, each of which is incorporated herein by reference in its entirety, can also be used in combination with quaternized organosilanes and/or quaternary ammonium compounds to produce synergistic antimicrobial compositions. We prefer to use Furanones 2, 19, 30 and 34. The chemical structures for these furanones are found in FIGS. 2, 5 and 6 of this application. Furanone compounds can be obtained from Unisearch Ltd., Kensington, New South Wales, Australia.

We have found that the most preferred furanone is Furanone 30 because it is generally active across a broad range of species of fungi and inhibits Gram positive bacteria. As an additional example, Furanones 26 and 27 also have shown synergistic antimicrobial activity when combined with a quaternized organosilane and a quaternary ammonium compound. The chemical structures of Furanones 26, 27 and 30 can be seen in FIGS. 4 and 5 of this application, and also in FIG. 2 of International Patent Publication No. WO 99/53915. Furanones 26 and 27 are often supplied as a mixture.

When used in conjunction with ethylenediamine-tetraacetic acid (EDTA) and/or other permeabilizing agents, furanones competitively inhibit the HSL, AHL-signaling/biofilm starvation response system in Gram-negative bacteria. By doing so, furanones inhibit growth and biofilm formation of Gram-negative bacteria. While Gram-positive bacteria do not have the same type of signaling system, these organisms nevertheless respond well to furanones even in the absence of permeabilizing agents.

Although furanones can be very selective in their inhibitory action, this does not mean that the synergistic antimicrobial compositions can only be formed with certain furanones. Rather, we believe that the activity of most if not all furanones can be synergistically enhanced by combining the furanone with a quaternary ammonium compound and/or a quaternized organosilane. In this way, it is generally possible to render effective furanones that otherwise are ineffective against certain microorganisms.

While we do not wish to be bound by our theory of molecular interaction and synergy, we believe that the quaternary ammonium, quaternized organosilane and furanone compounds can interact non-covalently in the synergistic antimicrobial composition. Each of the components is known to exhibit antimicrobial activity in its own right, although it was not known that they would exhibit unexpectedly high levels of synergy when combined in small amounts. When a quaternary ammonium compound, a quaternized organosilane and a furanone are combined, we theorize that the antimicrobial benefits of the quaternary ammonium compound and/or the quaternized organosilane are enhanced by the presence of the furanone. The use of quaternized organosilanes is known to impart residual antimicrobial properties to suitable surfaces. Quaternary ammonium compounds, however, tend to impart much weaker residual antimicrobial properties.

Consequently, a preferred formulation of the synergistic antimicrobial composition of the present invention might include the following components: Furanone 30, a quaternary ammonium compound such as BTC 1010 (didecyl dimethyl ammonium chloride)(80% active), and quaternized organosilane such as AEM 5772 Antimicrobial MUP which is 3-(trimethoxysilyl)-propyldimethyloctadecyl ammonium chloride at a 72% actives level (in methanol).

In yet another alternative embodiment, a furanone could be combined with a disinfectant amine (e.g., as sold by Lonza) or a biguanide (e.g., as sold by Avecia) to produce an effective antimicrobial composition. As before, sparing amounts of active ingredients should be used. The range of amounts of furanone to be used in this embodiment is the same as described in the earlier embodiment. Similarly, the range of amounts of disinfectant amine or biguanide to be used in this embodiment is in the same range as noted as regards the quaternary ammonium compound in the earlier embodiment. Accordingly, the earlier disclosure regarding component amounts should be consulted for both concentrated and non-concentrated products, and for "preferable", "more preferable", and "most preferable" amounts of furanone, and disinfectant amine or biguanide in an effective antimicrobial composition of this invention.

In addition to the compounds already described above, the following additional compounds may optionally be added to the synergistic antimicrobial composition in appropriate amounts known to those having ordinary skill in the art: water, sequestering or complexing agents (e.g., such as ethylenediamine-tetraacetic acid (EDTA)-based chelating agents, diethylenetriamine-pentaacetic acid (DTPA)-based chelating agents, N-(hydroxyethyl)-ethylenediamine-tetraacetic acid (HEDTA)-based chelating agents, nitrilotriacetic acid (NTA)-based chelating agents, or phosphonates, including salts, such as sodium, potassium, and monoethanolamine salts thereof), fragrance, additional disinfectants (e.g., such as phenolics, isothiazolins, iodofors, carbamates and hydantoins), and a pH adjuster such as sodium bicarbonate. The sequestering or complexing agents are advantageous since they tend to activate quaternary ammonium compounds.

The following Examples are merely illustrative of the present invention and are not to be considered as limiting the invention, which is properly delineated in the following claims. All parts and percentages expressed in the following Examples are by weight unless otherwise indicated.

EXAMPLE 1

Zone of Inhibition Assay Using Various Fungi

Fungi used: *Alternaria alternata, Aureobasidium pullulans, Cladosporium cladosporioides, Penicillium digitatum*

Method: Base formulas for A, B, C and D were prepared as described in Table 1 below.

TABLE 1

| Base Formulas for Screening Furanones without Added Furanone | A | B | C | D |
|---|---|---|---|---|
| Deionized Water (336701) | 95.00 | 92.70 | 93.00 | 94.70 |
| Plurafac B25-5 (non-ionic surfactant, biodegradable) | 5.00 | 5.00 | 5.00 | 5.00 |
| BTC 1010 (Didecyl dimethyl ammonium chloride)(80% active) | — | 2.00 | 2.00 | — |
| AEM 5772 Antimicrobial MUP (72% active) (3-(trimethoxysilyl) propyldimethyloctadecyl ammonium chloride) | — | 0.30 | — | 0.30 |
| Total | 100.00 | 100.00 | 100.00 | 100.00 |
| Note: Adjust pH to 8.25 with sodium bicarbonate (10% in water) | yes | yes | yes | yes |

Subsequently, test solutions were prepared either by: (1) taking a furanone or a base formula alone; or (2) by adding small amounts of suitably solubilized furanone (i.e., normally using ethanol) to a base formula so as to deliver a series of furanone concentrations in the test solutions (i.e., 10 ug/ml, 5 ug/ml, 1 ug/ml, 500 ng/ml, 100 ng/ml and 10 ng/ml). This resulted in a family of test solutions based on varying furanone concentrations. The various test solutions are set out at the left-hand margin of Tables 2A to 2D and can be described as follows:

Furanone 30 alone at decreasing concentrations, (denoted in Tables 2A to 2D as "30");

Furanones 26 and 27 as a mixture at decreasing concentrations (denoted in Tables 2A to 2D as "26/27");

Formula A alone without the addition of furanone (denoted in Tables 2A to 2D as "A");

Formula B alone without the addition of furanone (denoted in Tables 2A to 2D as "B");

Furanone 30 at decreasing concentrations, together with Formula A or Formula B (denoted in Tables 2A to 2D as "30+A" or "30+B"); and Furanones 26 and 27 as a mixture at decreasing concentrations, together with Formula A or Formula B (denoted in Tables 2A to 2D as "26/27+A" or "26/27+B").

Once the test solutions were prepared, 10 μl of each test solution was spotted onto TLC plates. The plates were overlaid with agar containing fungal spores. The TLC plates were incubated in a high humidity environment until growth could be observed visually. At inhibitory furanone concentrations, a zone of inhibition where no fungal growth was observed formed above the test solution spot. Lower furanone concentrations resulting in a zone of inhibition correspond to higher test solution efficacy.

Results: See Tables 2A, 2B, 2C and 2D set out below.

TABLE 2A

*Alternaria alternata*

|  | Zone of Inhibition with 10 μg/ml of Furanone (mm) | Zone of Inhibition with 5 μg/ml of Furanone (mm) | Zone of Inhibition with 1 μg/ml of Furanone (mm) | Zone of Inhibition with 500 ng/ml of Furanone (mm) | Zone of Inhibition with 100 ng/ml of Furanone (mm) | Zone of Inhibition with 10 ng/ml of Furanone (mm) |
|---|---|---|---|---|---|---|
| 30 | 40–42 | 35–37 | 15–10 | 3–4 | 2–3 | 0 |
| 30 + A | 39–40 | 32–33 | 12–15 | 2 | 0 | 0 |
| 30 + B | 8–10.5 | 10.5 | 7–9 | 9–10 | 9–10 | 8–10 |
| 26/27 | 26–27 | 10–15 | 0 | 0 | 0 | 0 |
| 26/27 + A | 25 | 5–12 | 0 | 0 | 0 | 0 |
| 26/27 + B | 7–9.5 | 10 | 8–10 | 9.5–10 | 9.5 | 10 |
| A | 0 | 0 | 0 | 0 | 0 | 0 |
| B | 0 | 0 | 0 | 0 | 0 | 0 |

TABLE 2B

*Aureobasidium pullulans*

|  | Zone of Inhibition with 10 μg/ml of Furanone (mm) | Zone of Inhibition with 5 μg/ml of Furanone (mm) | Zone of Inhibition with 1 μg/ml of Furanone (mm) | Zone of Inhibition with 500 ng/ml of Furanone (mm) | Zone of Inhibition with 100 ng/ml of Furanone (mm) | Zone of Inhibition with 10 ng/ml of Furanone (mm) |
|---|---|---|---|---|---|---|
| 30 | 15–17 | 3–10 | 0 | 0 | 0 | 0 |
| 30 + A | 12–13 | 3–7 | 0 | 0 | 0 | 0 |
| 30 + B | 10 | 8.5–9.5 | 9.5–10 | 7.5–9.5 | 10 | 10 |
| 26/27 | 12–13 | 10–7 | 0–5 | 0 | 0 | 0 |
| 26/27 + A | 5–9 | 3–7 | 2 | 0 | 0 | 0 |
| 26/27 + B | 8–10 | 9–10 | 9.5 | 8.5–9.5 | 10 | 9.5–10 |
| A | 0 | 0 | 0 | 0 | 0 | 0 |
| B | 0 | 0 | 0 | 0 | 0 | 0 |

TABLE 2C

*Cladosporium cladosporioides*

|  | Zone of Inhibition with 10 μg/ml of Furanone (mm) | Zone of Inhibition with 5 μg/ml of Furanone (mm) | Zone of Inhibition with 1 μg/ml of Furanone (mm) | Zone of Inhibition with 500 ng/ml of Furanone (mm) | Zone of Inhibition with 100 ng/ml of Furanone (mm) | Zone of Inhibition with 10 ng/ml of Furanone (mm) |
|---|---|---|---|---|---|---|
| 30 | 42–56 | 40–45 | 20–30 | 20–21 | 9–10 | 0 |
| 30 + A | 35–39 | 30–37 | 17–19 | 15–16 | 2–3 | 0 |
| 30 + B | 10 | 9.5–10 | 8.5–9.5 | 10 | 8.5–10 | 8.5–9 |

TABLE 2C-continued

*Cladosporium cladosporioides*

| | Zone of Inhibition with 10 μg/ml of Furanone (mm) | Zone of Inhibition with 5 μg/ml of Furanone (mm) | Zone of Inhibition with 1 μg/ml of Furanone (mm) | Zone of Inhibition with 500 ng/ml of Furanone (mm) | Zone of Inhibition with 100 ng/ml of Furanone (mm) | Zone of Inhibition with 10 ng/ml of Furanone (mm) |
|---|---|---|---|---|---|---|
| 26/27 | 30–32 | 25–27 | 12–20 | 0 | 0 | 0 |
| 26/27 + A | 22–24 | 15–20 | 9–11 | 0 | 0 | 0 |
| 26/27 + B | 9.5–10 | 8–9 | 8–10 | 10 | 9.5 | 9.5–10 |
| A | 0 | 0 | 0 | 0 | 0 | 0 |
| B | 0 | 0 | 0 | 0 | 0 | 0 |

TABLE 2D

*Penicillium digitatum*

| | Zone of Inhibition with 10 μg/ml of Furanone (mm) | Zone of Inhibition with 5 μg/ml of Furanone (mm) | Zone of Inhibition with 1 μg/ml of Furanone (mm) | Zone of Inhibition with 500 ng/ml of Furanone (mm) | Zone of Inhibition with 100 ng/ml of Furanone (mm) | Zone of Inhibition with 10 ng/ml of Furanone (mm) |
|---|---|---|---|---|---|---|
| 30 | 32–45 | 32–30 | 12–15 | 10–19 | 0 | 0 |
| 30 + A | 25–45 | 20–35 | 5–10 | 0 | 0 | 0 |
| 30 + B | 8–10 | 9–10 | 10 | 8–10 | 8–10 | 10 |
| 26/27 | 30–32 | 15–20 | 10–20 | 0 | 0 | 0 |
| 26/27 + A | 10–30 | 5 | 0–2 | 0 | 0 | 0 |
| 26/27 + B | 10 | 8–10 | 9.5–11 | 10 | 9.5–10.5 | 10 |
| A | 0 | 0 | 0 | 0 | 0 | 0 |
| B | 0 | 0 | 0 | 0 | 0 | 0 |

Comments: When observing the test results in Tables 2A–2D, it is important to recognize that a larger zone does not necessarily mean greater antimicrobial activity. This is because the size of the zone of inhibition is a function of the solubility of the composition in question. What is relevant and revealing about the test results is the concentration at which the zone of inhibition continues to appear. By this analysis, the test solutions containing a furanone (i.e., either Furanone 30 or Furanones 26 and 27) in combination with a quaternary ammonium compound (i.e., BTC 1010) and a quaternized organosilane (i.e., AEM 5772 Antimicrobial MUP) were most antimicrobially effective. Although the test furanones appeared to be antimicrobially effective on their own at higher tested concentrations, this was not the case with Formula B which contained a quaternized organosilane and a quaternary ammonium compound.

A comparison between the results for Furanone 30 alone and Furanone 30+ Formula A reveals that the latter is generally less potent than the former. This is because the addition of a nonionic surfactant tends to quench the antimicrobial activity of a composition even though it is extremely helpful in cleaning (as opposed to disinfecting).

EXAMPLE 2

Effectiveness of Inventive Composition Against *Staphylococcus aureus*

Purpose: To demonstrate the effectiveness of the inventive composition comprising a furanone, a quaternized organosilane and a quaternary ammonium compound against *Staphylococcus aureus*, compared to that of a quaternized organosilane or a furanone alone, or a quaternized organosilane in combination with a quaternary ammonium compound.

Method: Formulas were prepared as described in Table 3 set out below.

TABLE 3

| | Formula E Quaternized organosilane | Formula F Quaternized + Quaternary ammonium compound | Formula G Furanone | Formula H Furanone + Quaternized Organosilane + Quaternary Ammonium Compound |
|---|---|---|---|---|
| Deionized Water | to 100% | to 100% | to 100% | to 100% |
| Isopropanol | 10.000 | 10.000 | 10.000 | 10.000 |
| AEM 5772 Antimicrobial MUP (72%) (Quaternized Organosilane) | 0.150 | 0.150 | 0 | 0.150 |
| BTC 2125M (80%) (Blend of benzalkonium chloride and ethyl-benzalkonium chloride) | 0 | 0.270 | 0 | 0.270 |
| Furanone 30 1.0% solution in ethanol (weight/volume) | 0 | 0 | 0.00001% (0.1 ml) (equivalent to adding 0.001 g) | 0.00001% (0.1 ml) (equivalent to adding 0.001 g) |
| Total | 100.000 | 100.000 | 100.000 | 100.000 |

Sterile glass microscopy slides were dipped into the above Formulas E, F, G and H. Excess solution was allowed to drain off. When thoroughly dry, the slides were hung into large, sterile beakers filled with 800 ml of trypticase soy broth and also containing a magnetic stir bar. Each beaker held eight identically coated slides. An additional beaker contained eight untreated sterile slides as controls. The beakers were placed on a multiposition magnetic stir plate and inoculated with 1 ml of an overnight culture of *Staphylococcus aureus*.

Results: The beaker containing slides dipped into Formulas E and G and the untreated control showed cell growth (turbidity) when examined after 16 hours. The beakers with slides dipped into Formulas F and H (i.e., Beakers F and H) were clear at that time. Beaker F was slightly turbid after 24 hours while Beaker H remained clear. The next morning, at 41 hours, all beakers except Beaker H were extremely turbid. Beaker H was slightly turbid at this time. At 48 hours, any discernible differences between the beakers had disappeared.

Conclusions: This experiment yields the following conclusions:
1. A furanone and a quaternized organosilane alone (Formulas G and E) were unable to hold down bacterial growth at very low concentrations. (The amount adsorbed onto the glass slides is not known).
2. The two formulations (Formulas F and H) containing a quaternized organosilane and a quaternary ammonium compound were able to delay bacterial growth.
3. Formula H, containing furanone in addition to a quaternized organosilane and a quaternary ammonium compound, was able to delay bacterial growth longer than Formula F without furanone.

EXAMPLE 3

Zone of Inhibition Assay Using *Staphylococcus aureus*

Organism used: *Staphylococcus aureus*

Method: A sterile filter paper was placed on an agar plate (TSA) and inoculated with 1 ml of a diluted (10%) overnight culture of *Staphylococcus aureus*. One side of a glass slide (1"×2") was wetted with formulations E, F, G or H as prepared in accordance with the formulations in Table 3 (set out in Example 2).

Figure 1B:
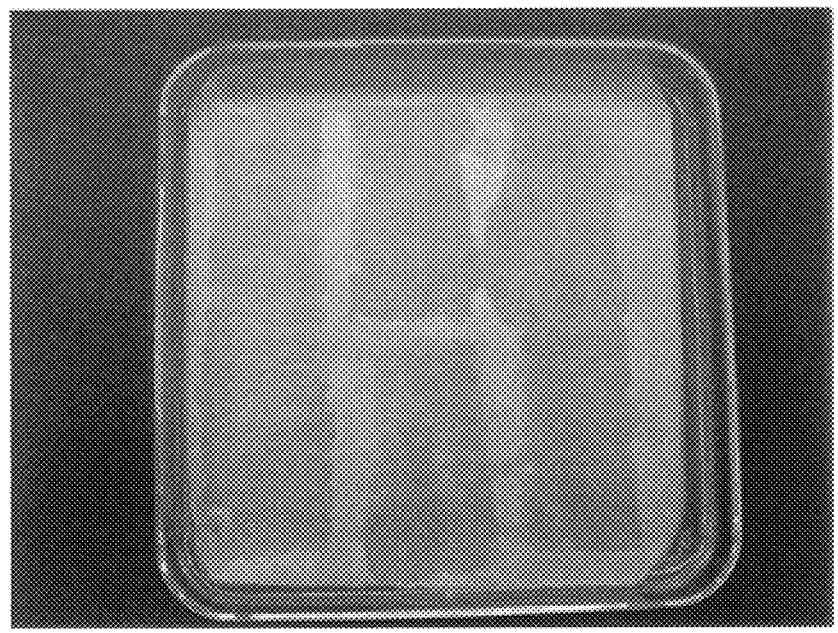
Figure 1C:
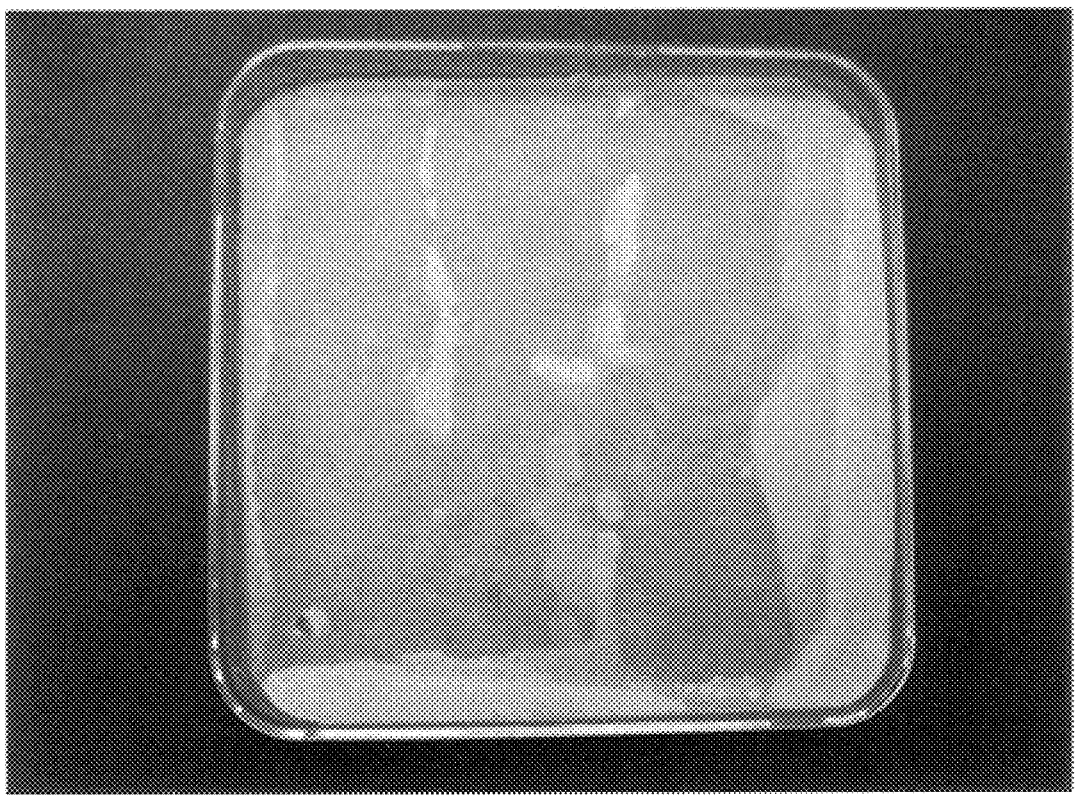
Figure 2:
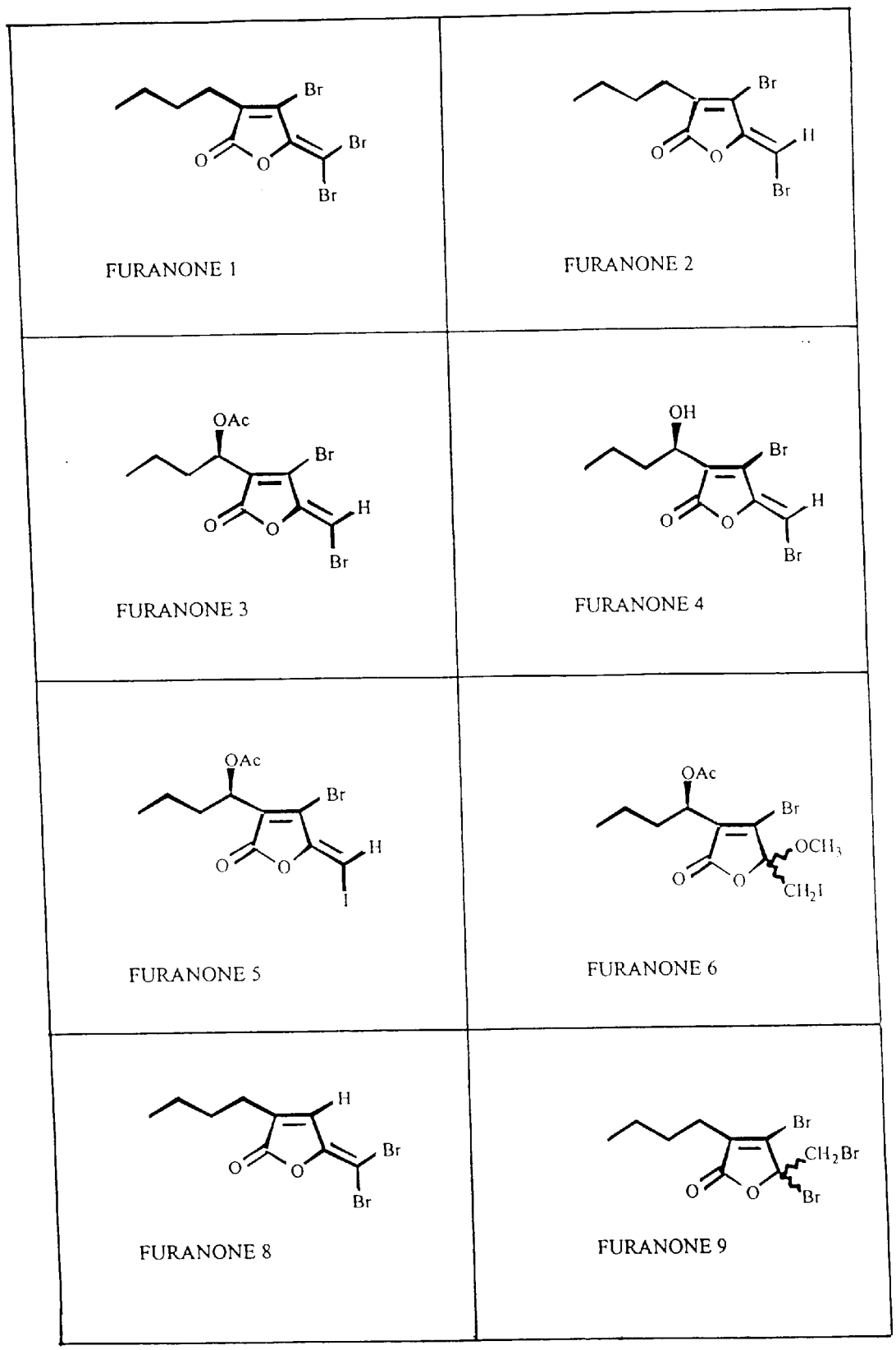
FIGS. 2–8 depict chemical structures of various furanones that could be used in the inventive synergistic antimicrobial composition described herein.
Figure 3:
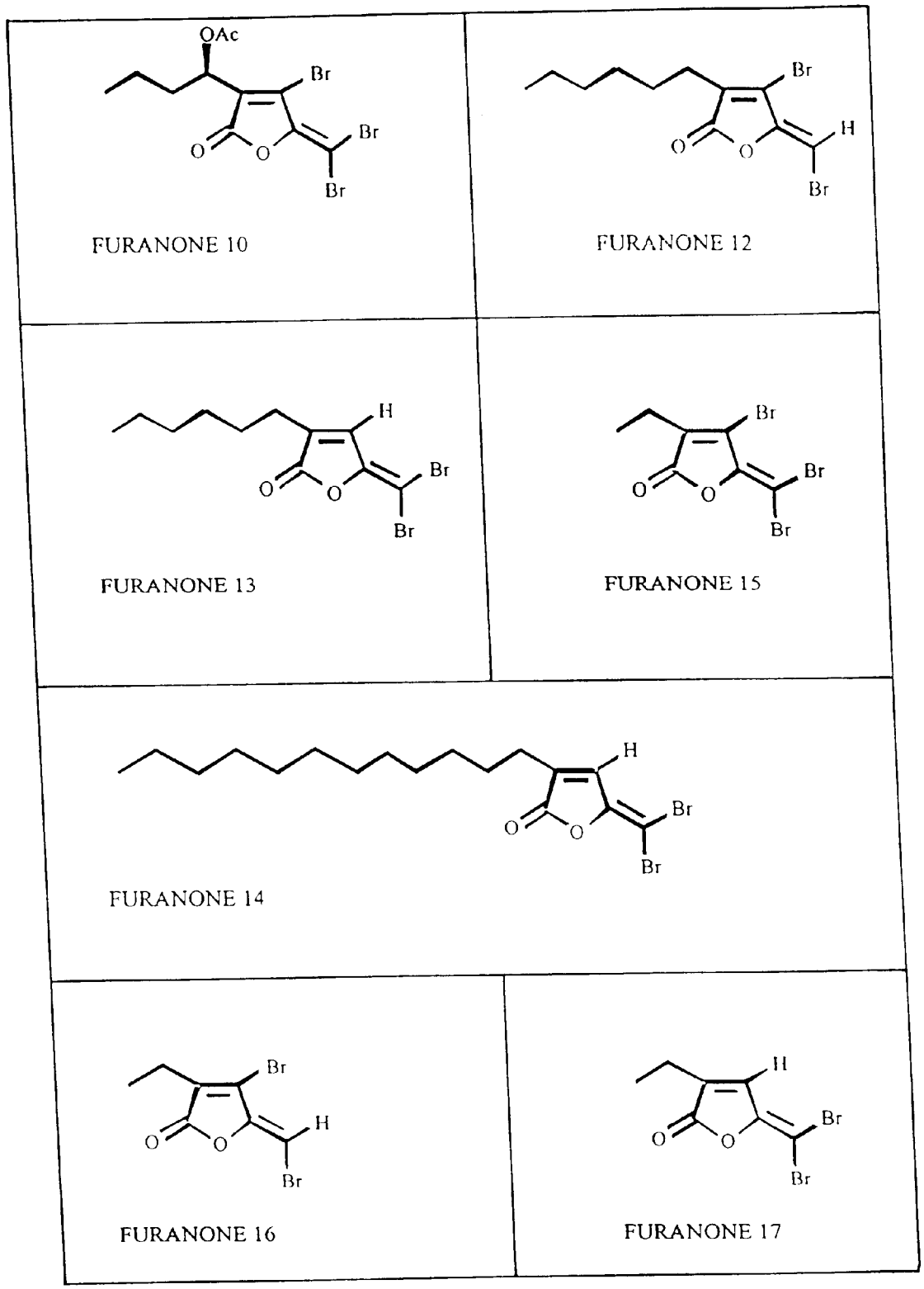
Figure 4:
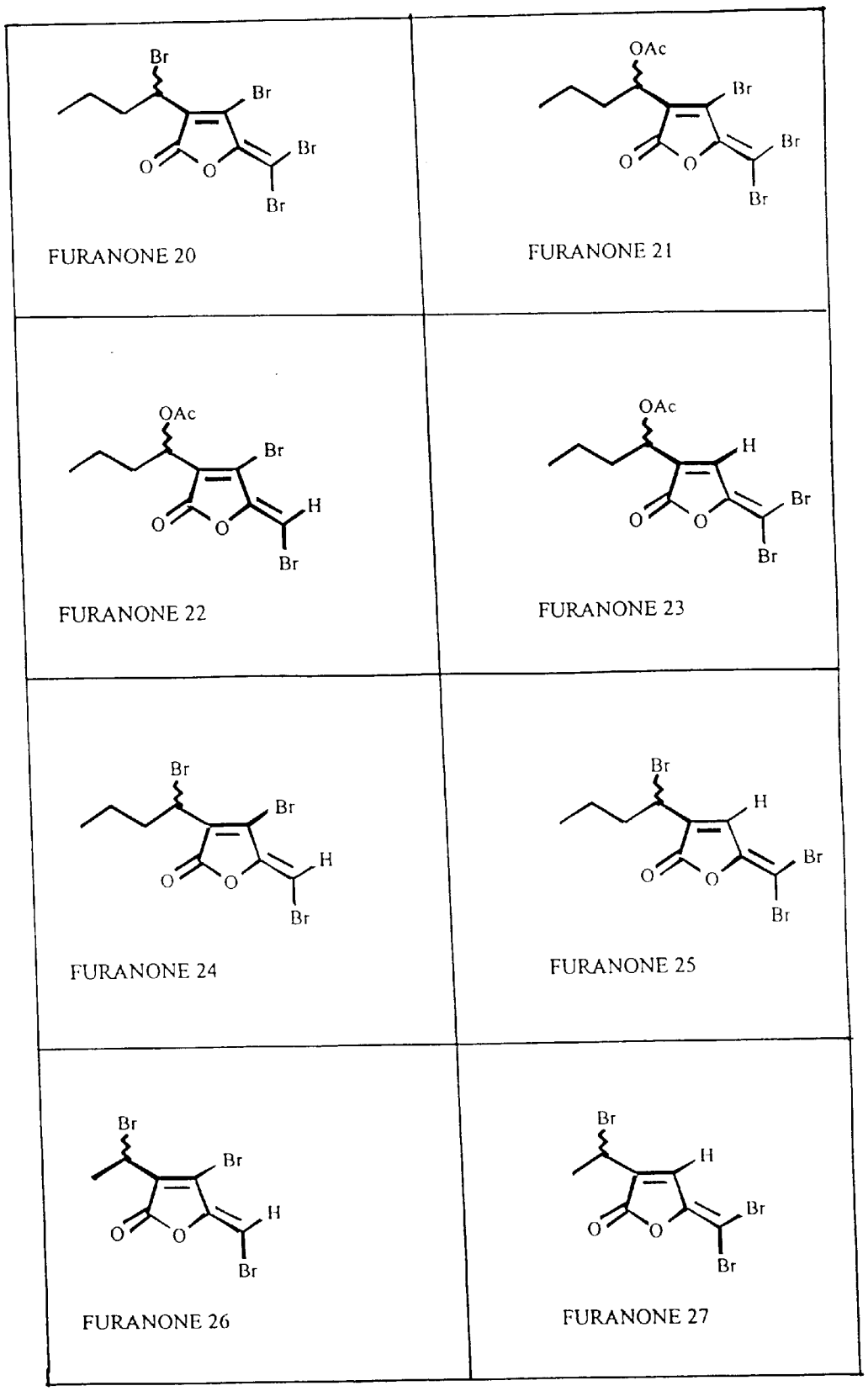
Figure 5:
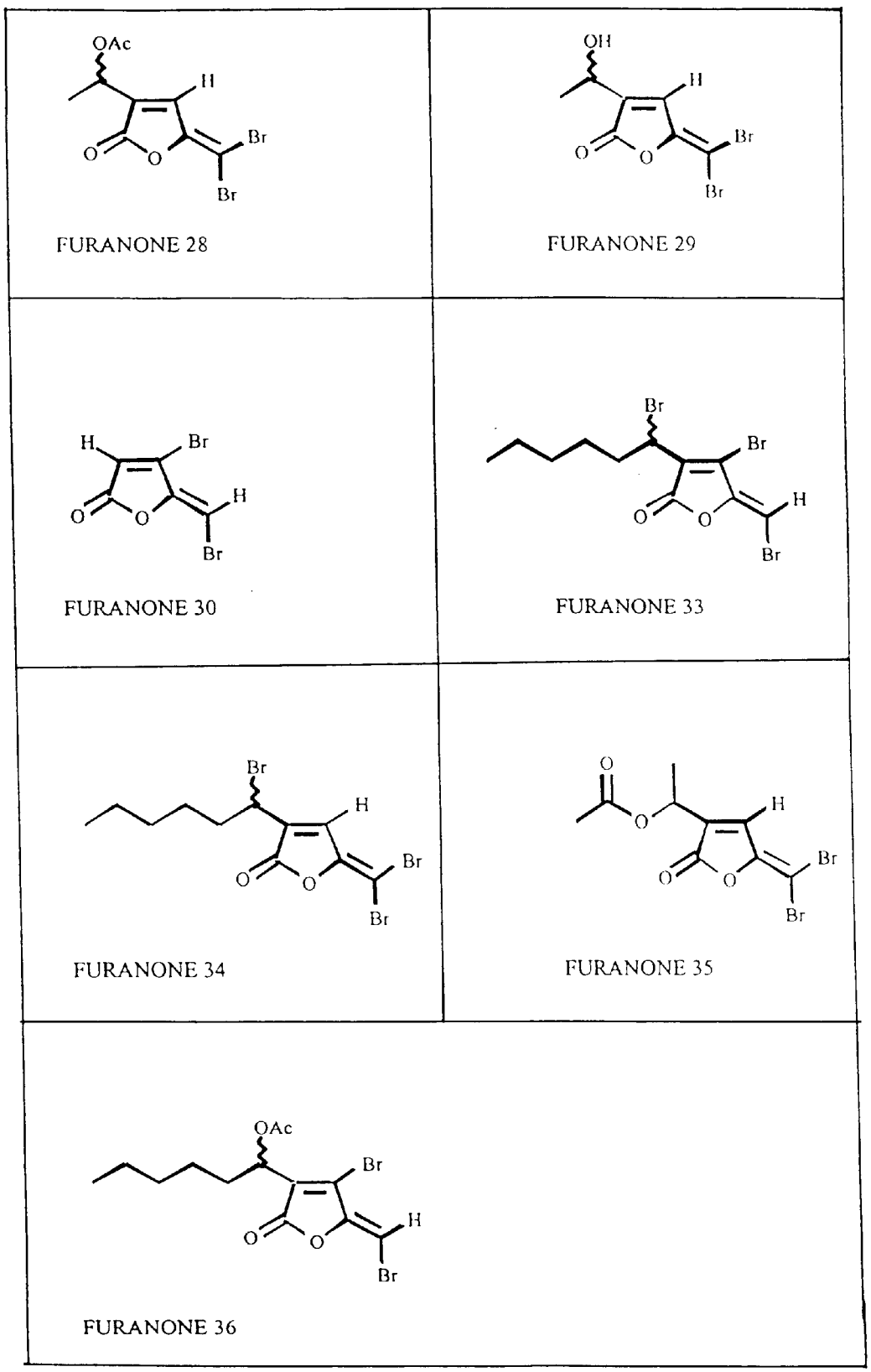
Figure 6:
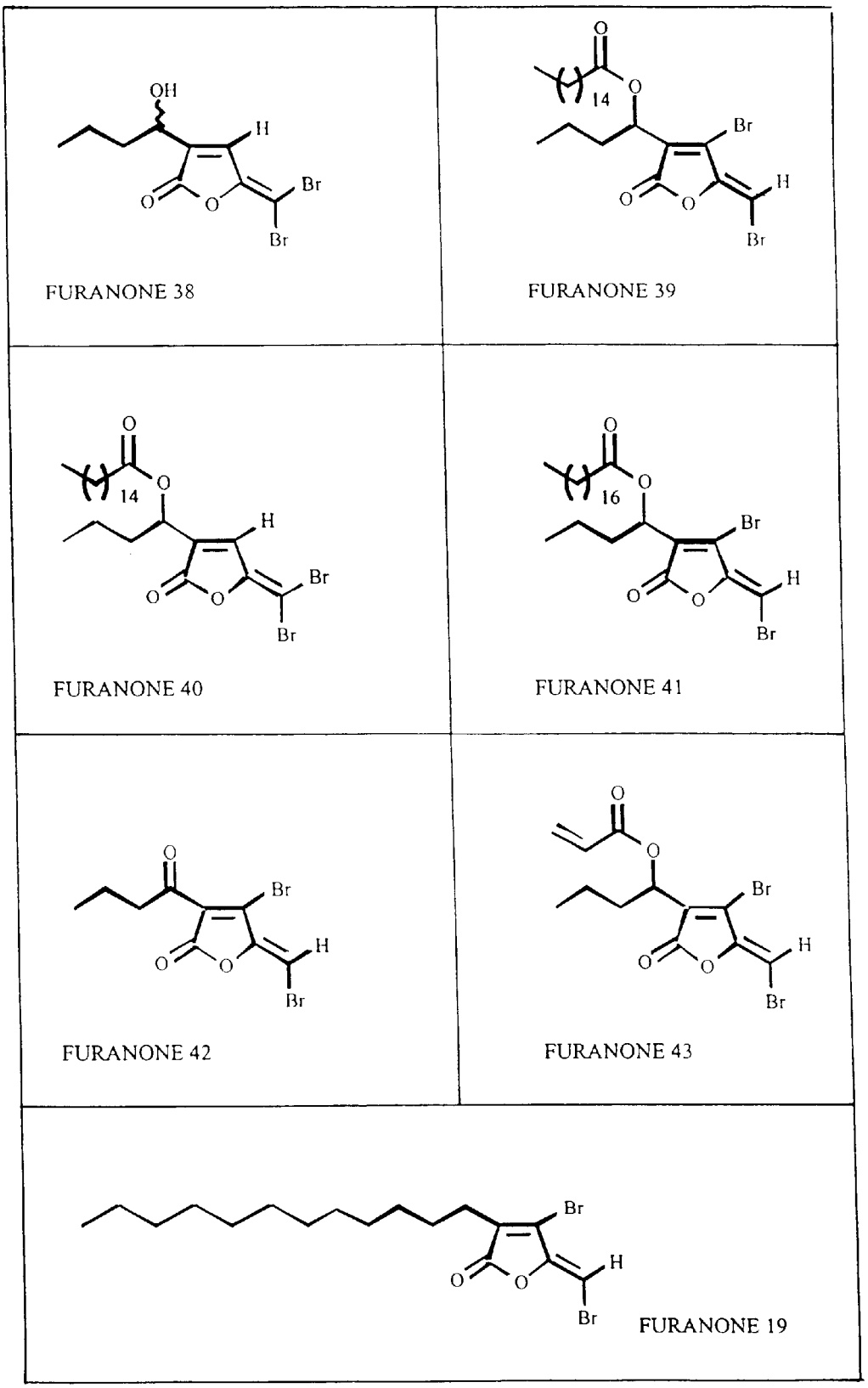
Figure 7:
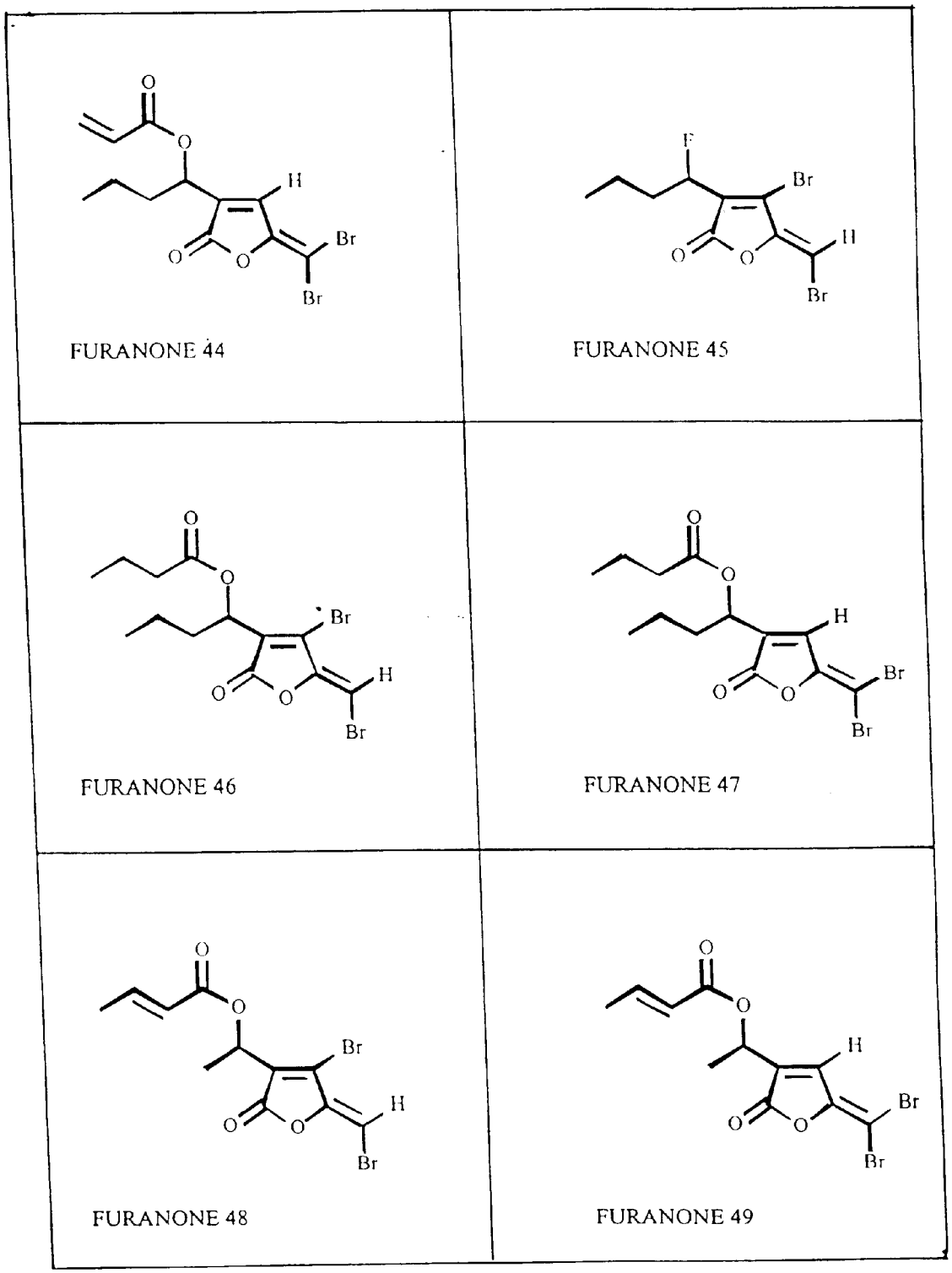
Figure 8:
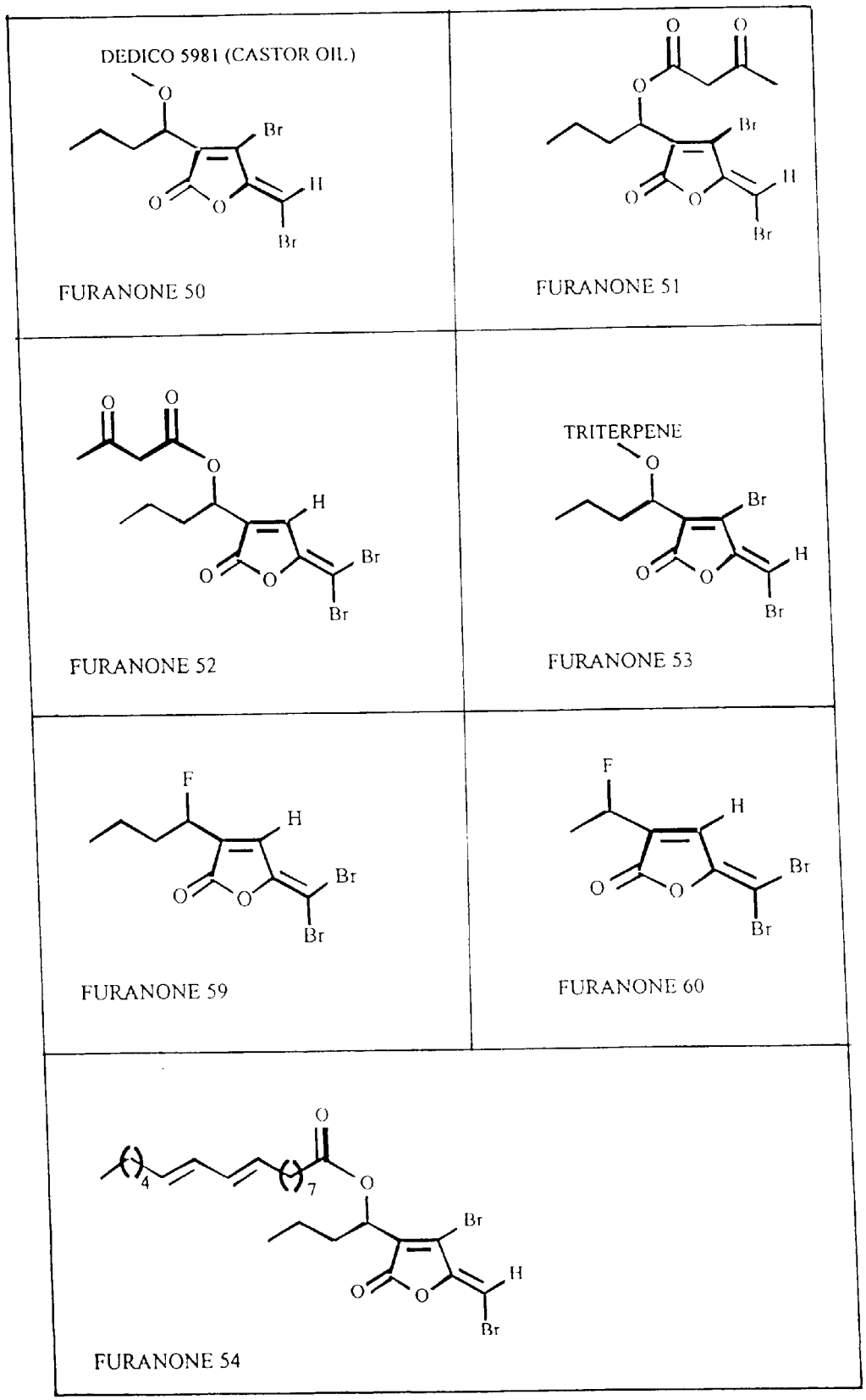

Six slides were prepared in this way for each of formulations E, F, G and H. Surplus solution was allowed to drain off and the slides were allowed to dry. The dry slides were then placed in groups of 6 (grouped by formulation) and placed with the treated side down onto the inoculated filter papers. A control plate was also prepared with six untreated glass slides being placed onto inoculated filter papers. A thick bacterial lawn developed on the filter paper between the slides. Zones of inhibition formed around the slides where inhibitory activity was caused by the formulations. The extent of the bacteria-free zone around the slides provides a good indication of treatment efficacy of a particular formulation. By these criteria, Formulation H (containing quaternary ammonium compound, quaternized organosilane and furanone) shown in FIG. 1C shows the greatest zone of inhibition around the plate. FIG. 1A shows no zone of inhibition for the control plate containing untreated glass slides. The plates containing slides treated with Formulation E (containing quaternized organosilane only) and Formulation G (containing furanone only) also had no zone of inhibition, and appeared essentially as seen in FIG. 1A for the controls. FIG. 1B shows slight zones of inhibition around the glass slides treated with Formulation F (containing quaternary ammonium compound and quaternized organosilane). (See photographic images in FIGS. 1A to 1C which show zones of inhibition.)

Results: The largest zone of inhibition appeared on the slide shown in FIG. 1C that previously had been treated with a composition containing quaternary ammonium compound, a quaternized organosilane and a furanone. In this case, the size of the zone of inhibition may be directly linked to efficacy, as the concentrations of the test solutions are very much alike, and so the test solutions should not differ significantly with respect to their solubilities. Therefore, the widest zone of inhibition is indicative of the greatest efficacy.

EXAMPLE 4

Zone of Inhibition Assay Using *Aspergillus niger*

Organism used: *Aspergillus niger*

Method: Test formulations were prepared as shown in Table 3 set out above.

To create a test surface, 5 $\mu$l of each test material was applied to the center of a 2.5×2.5 cm piece of a flexible silica gel TLC plate (Whatman PE SilG, 250 micrometer layer, Catalog #4410-221). The samples were allowed to dry for 30 minutes and then placed gel side up in the middle of an 88 mm Petri dish containing about 10 ml of 2% water agar as a source of moisture during incubation. Six drops of a suspension of *Aspergillus niger* in molten potato dextrose agar (PDA) was applied to the surface of the TLC plate. The plates were incubated at 28° C. for 10 days with observations taken periodically throughout this period.

Observations:

Day 2:

Formulas E and G showed no effect. The *Aspergillus niger* spores germinated and growth covered the entire surface of the TLC plate, including the test surface.

Formulas F and H resulted in a clear zone of inhibition above the test surface where test material was applied. No spores had germinated in the agar above the treatments.

Day 7:

Formulas E and G were totally overgrown and no effect of the treatments could be observed.

Formula F still showed where the zone of inhibition had occurred previously, although the fungi had clearly started to germinate and fungal growth could be observed. This growth was less dense than over the untreated portion of the test surface.

Formula H still showed a clear zone of inhibition.

Conclusion: This experiment confirms that the inventive composition comprising a furanone, a quaternized organosilane and a quaternary ammonium compound is effective in inhibiting fungal growth, particularly the growth of *Aspergillus niger*.

Industrial Applicability

This invention has applicability to a variety of industrial and household cleaners intended to inhibit the growth of fungi (mold and mildew) and bacteria on surfaces, and in reservoirs or conduits that are fluid-filled. For example, this invention is useful for toilet cleaners, bathroom and shower cleaners, kitchen cleaners, floor cleaners and drain cleaners. Other applications may include treatment of furnishings and fabrics, water circulating systems, air ducts, building materials, outdoor structures and the exteriors of ships. The inventive composition can be prepared in a concentrated or regular strength format for both domestic and industrial use. The benefits to the consumer of using the synergistic antimicrobial composition of this invention is that surfaces stay clean longer, growth of bacteria, mold and biofilm is inhibited, and treated surfaces are easier to clean. Environmental benefits result from the overall lower use of active ingredients.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

We claim:

1. A composition comprising:
   (a) a sparing amount of at least one furanone;
   (b) a sparing amount of at least one quaternized organosilane; and
   (c) a sparing amount of at least one quaternary ammonium compound,
   wherein the amount of each of components (a), (b) and (c) is sufficient to form, in combination, a synergistic antimicrobial composition.

2. The composition of claim 1, wherein the sparing amount of furanone is between about 1 $\mu$g/L and about 5000 mg/L of the composition.

3. The composition of claim 1, wherein the sparing amount of quaternized organosilane is between about 0.001 weight percent and about 5.0 weight percent of the composition.

4. The composition of claim 1, wherein the sparing amount of quaternary ammonium compound is between about 0.01 weight percent and about 10.0 weight percent of the composition.

5. The composition of claim 1, wherein the composition is effective against microorganisms selected from the group consisting of a fungus, a yeast, a bacterium, and mixtures thereof.

6. The composition of claim 5, wherein the fungus is selected from the group consisting of *Alternaria alternata, Aureobasidium pullullans, Cladosporium cladosporioides* and *Penicillium digitatum.*

7. The composition of claim 5, wherein the yeast is *Candida albicans.*

8. The composition of claim 5, wherein the bacterium is *Staphylococcus aureus.*

9. The composition of claim 1, wherein the at least one furanone is Furanone 30.

10. The composition of claim 1, wherein the at least one quaternized organosilane is selected from the group consisting of 3-(trimethoxysilyl)propyldimethyl-octadecyl ammonium chloride and 3-(trimethoxysilyl)propylmethyl-di(decyl) ammonium chloride.

11. The composition of claim 1, wherein the at least one quaternary ammonium compound is selected from the group consisting of didecyl dimethyl ammonium chloride, dioctyl dimethyl ammonium chloride, octyl decyl dimethyl ammonium chloride, benzalkonium chloride and alkyl benzyl alkyl dimethyl ammonium chloride.

12. The composition of claim 1, further comprising one or more ingredients selected from the group consisting of: water, a sequestering or complexing agent, a fragrance, an additional disinfectant, and a pH adjustor.

13. A method of cleaning a surface, or a reservoir or conduit that is fluid-filled comprising:
    providing a synergistic antimicrobial composition comprising:
    (a) a sparing amount of at least one furanone;
    (b) a sparing amount of at least one quaternized organosilane; and
    (c) a sparing amount of at least one quaternary ammonium compound; and
    applying the composition to the surface, reservoir, or conduit to be cleaned.

14. The method of claim 13, wherein the sparing amount of the at least one furanone is between about $1.0 \times 10^{-7}$ weight percent and about 0.5 weight percent of the composition.

15. The method of claim 13, wherein the sparing amount of the at least one quaternized organosilane is between about 0.001 weight percent and about 5.0 weight percent of the composition.

16. The method of claim 13, wherein the sparing amount of the at least one quaternary ammonium compound is between about 0.01 weight percent and about 10.0 weight percent of the composition.

17. The method of claim 13, wherein the at least one furanone is Furanone 30.

18. The method of claim 13, wherein the at least one quaternized organosilane is 3-(trimethoxysilyl)propyl-dimethyl-octadecyl ammonium chloride.

19. The method of claim 13, wherein the at least one quaternary ammonium compound is selected from the group consisting of didecyl dimethyl ammonium chloride and benzalkonium chloride.

* * * * *